United States Patent [19]

Carroll et al.

[11] Patent Number: 5,025,172
[45] Date of Patent: Jun. 18, 1991

[54] CLOCK GENERATOR GENERATING TRAPEZOIDAL WAVEFORM

[75] Inventors: Kenneth J. Carroll, San Jose; Benjamin D. Pless, Menlo Park, both of Calif.

[73] Assignee: Ventritex, Inc., Sunnyvale, Calif.

[21] Appl. No.: 476,932

[22] Filed: Feb. 8, 1990

Related U.S. Application Data

[62] Division of Ser. No. 354,632, May 19, 1989.

[51] Int. Cl.$^5$ .......................... H03K 5/00; H03K 5/13
[52] U.S. Cl. .................... 307/261; 307/269; 307/263; 307/582; 328/182; 328/185
[58] Field of Search ............... 307/269, 481, 261, 582, 307/263; 328/181, 183, 185

[56] References Cited

U.S. PATENT DOCUMENTS

| | | | |
|---|---|---|---|
| 3,621,281 | 11/1971 | Hagen | 328/181 |
| 3,879,683 | 4/1975 | Bosselaers | 328/181 |
| 4,282,549 | 8/1981 | Balaban et al. | 307/269 |
| 4,322,636 | 3/1930 | Schroder | 328/181 |
| 4,717,848 | 1/1988 | Rabaey et al. | 307/261 |

Primary Examiner—Stanley D. Miller
Assistant Examiner—Richard Roseen
Attorney, Agent, or Firm—Gerstman & Ellis, Ltd.

[57] ABSTRACT

An implantable cardiac defibrillator employing a switched capacitor filter stage having charge steering resistors connected in series with corresponding switched capacitors that are coupled to a sensitive node of an operational amplifier. The stored channel charges in associated switches when they are tuned off are directed away from the sensitive node. The switches associated with the switched capacitors are operated by control signals having a generally trapezoidal shaped waveform so as to slowly turn off the same, thereby reducing clock feedthrough and charge injection induced offset voltage on the output of the operational amplifier.

6 Claims, 4 Drawing Sheets

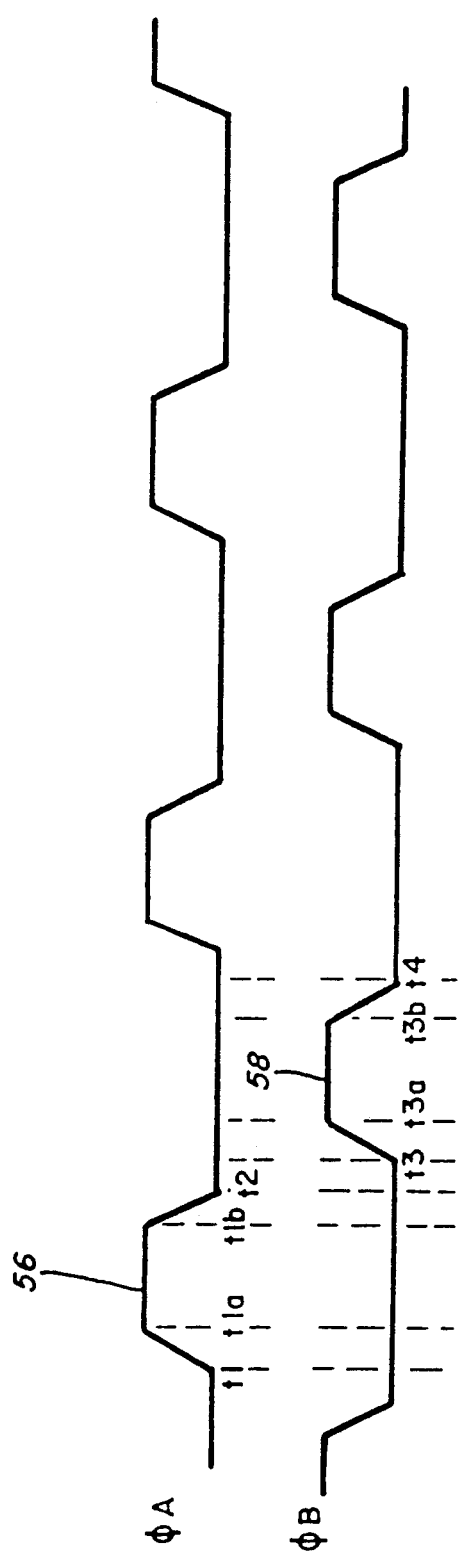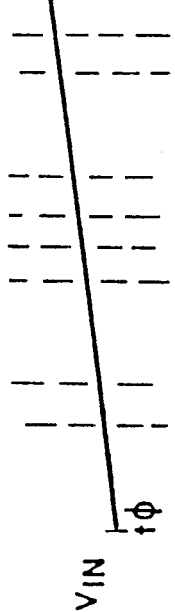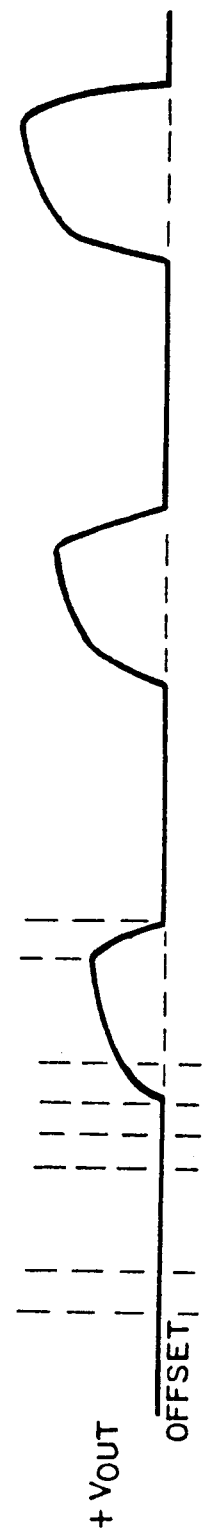
FIG. 3a
FIG. 3b
FIG. 3c
FIG. 3d

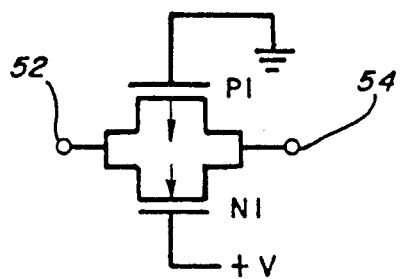
FIG. 4 CHARGE STEERING RESISTOR
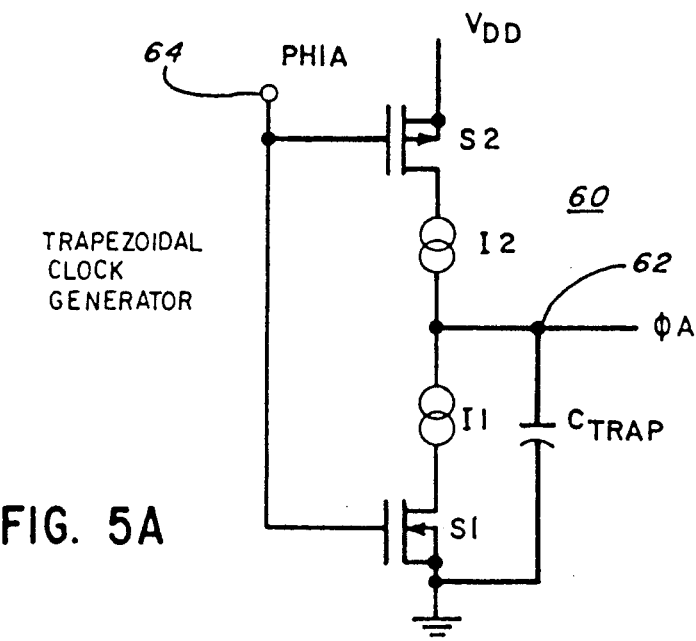
FIG. 5A
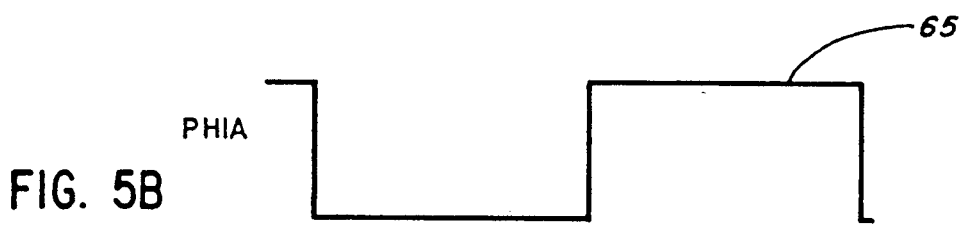
FIG. 5B
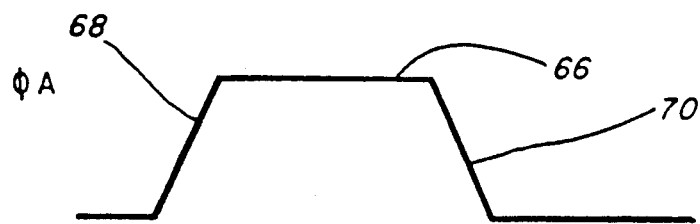
FIG. 5C

CLOCK GENERATOR GENERATING TRAPEZOIDAL WAVEFORM

This is a division of application Ser. No. 354,632, filed May 19, 1989.

BACKGROUND OF THE INVENTION

This invention relates generally to implantable medical devices and more particularly, it relates to an implantable cardiac defibrillator employing a switched capacitor filter stage which includes a switch structure so as to produce a low charge-injection induced offset voltage on the output of an operational amplifier. In particular, the present invention is directed to an implantable cardiac defibrillator device which utilizes the present switched capacitor filter stage for processing heart signals from the atrium and/or ventricle.

In recent years, there has been substantial progress made in the research and development of defibrillating devices for providing an effective medical response to various disorders, such as ventricular fibrillation. Research effort has also been made toward developing improved sensing techniques for reliably monitoring heart activity so as to determine when a defibrillating high energy shock is required. However, the implantable cardiac defibrillators of the prior art used comparatively simple sensing circuits. These prior art sensing circuits would typically include switched capacitor circuits.

In general, switched capacitor circuits combine switches implemented with a pair of CMOS transistors and capacitors where the transistors are controlled by true and complementary clock pulse signals. When the switched capacitor circuits are used to construct a switched capacitor filter stage containing an operational amplifier there is suffered the disadvantage of creating a charge-injection induced offset voltage on the output of the operational amplifier when the switch transistors are turned off. This is caused by charge injection due to carriers released from the channel and to coupling through gate-to-diffusion overlap capacitances. For the purposes of completeness, reference is made to an article entitled "Charge Injection in Analog MOS Switches" by George Wegmann, Eric A. Vittoz and Fouad Rahali in *IEEE Journal of Solid State Circuits*, Vol. SC-22 No. 6, December, 1987, pp. 1091–1097, which discusses in detail the switch induced charge injection problems. It would therefore be desirable to provide a switched capacitor filter stage which reduces or eliminates the problem of charge-injection induced offset voltage associated with the output of an operational amplifier.

The present invention provides an implantable cardiac defibrillator employing a switched capacitor filter stage which includes a unique switch structure so as to produce a low charge-injection induced offset voltage on the output of an operational amplifier. This is achieved by inserting MOS charge steering resistors in series with the capacitors that are coupled to a sensitive node of the operational amplifier. As a result, the stored channel charges tend to flow to the low impedance node, that is directed away from the sensitive nodes, thereby reducing the effect of charge injection when the transition of the leading and trailing edges of the clock pulse signals that control the switching transistors are slowed down. For purposes of completeness, reference is made to an article entitled "High Resolution Switched Capacitor D/A Converter" by Roubik Gregorian in *Microelectronics Journal*, Vol. 12, No. 2, 1981, pp. 10–13, where the basic switched capacitor configuration, in non-filtering form, is presented.

SUMMARY OF THE INVENTION

Accordingly, it is a general object of the present invention to provide an implantable medical device employing an improved switched capacitor filter stage which has a low charge-injection induced offset voltage.

It is an object of the present invention to provide an implantable medical device employing an improved switched capacitor filter stage which includes a unique switch structure and trapezoidal clock signals so as to produce a low charge-injection induced offset voltage on the output of an operational amplifier, thereby improving its accuracy.

It is another object of the present invention to provide an implantable medical device employing a switched capacitor filter stage wherein MOS charge steering resistors are inserted in series with capacitors that are coupled to a sensitive node of an operational amplifier and trapezoidal clock signals are used, thereby reducing charge-injection induced offset voltage.

It is still another object of the present invention to provide an implantable medical device which includes a clock waveform generator for producing control signals having a trapezoidal waveform.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIG. 3(*a*)–3(*d*) are waveform diagrams useful in understanding the operation of FIG. 1;

FIG. 4 shows the implementation of the charge steering resistor using a pair of MOS transistors;

FIG. 5(*a*) is a schematic circuit diagram of a trapezoidal waveform generator for producing the control signal $\phi A$;

FIG. 5(*b*) illustrates a pulse of the clock pulse PH1A; and

FIG. 5(*c*) illustrates a pulse of the control signal $\phi A$, which has been enlarged over the ones of FIG. 3(*a*).

DESCRIPTION OF THE PREFERRED EMBODIMENT

The description of the preferred embodiment begins with the description of FIG. 5A below.

Figure 1:
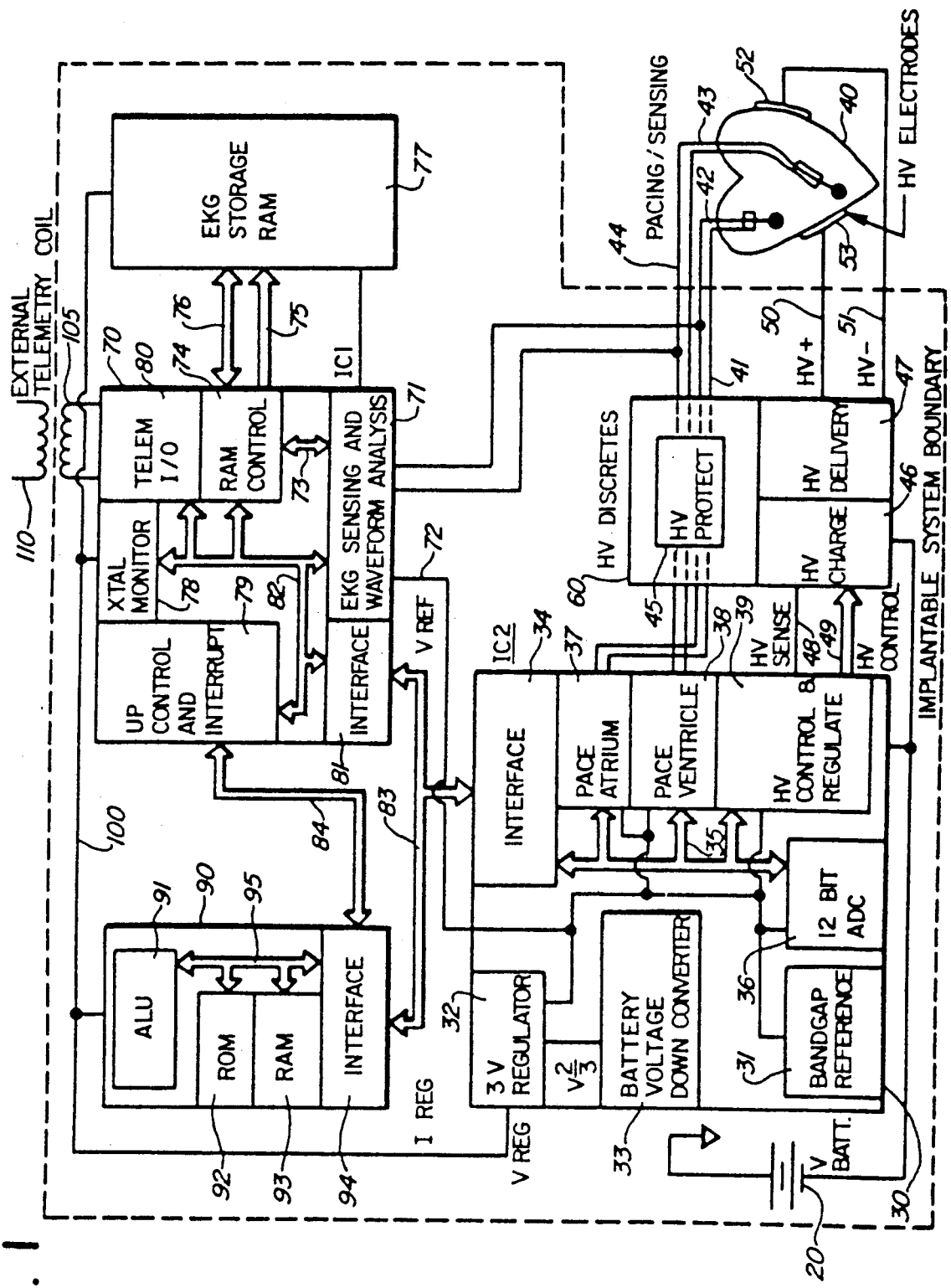
FIG. 1 is a block diagram of an implantable cardiac defibrillator, constructed in accordance with the principles of the present invention.

In FIG. 1, there is illustrated in a functional block diagram format the internal and external elements of an implantable cardiac defibrillator constructed in accordance with the principles of the present invention. A detailed description of the elements of FIG. 1 as well as their interconnection and operation has been presented in co-pending application Ser. No. 07/354,632, entitled "Method for Cardiac Defibrillation" and assigned to the same assignee as the present invention, which is hereby incorporated by reference. Thus, the detailed description will not herein be repeated. However, a general description of the elements of FIG. 1 required for an understanding of the present invention will be presented.

In particular, FIG. 1 shows an implantable cardiac defibrillator which includes four integrated circuit chips IC1-IC4 and a set of high voltage discrete component blocks 45-47. The block 45 contains high voltage protection circuits which prevent the atrium and ventricle pacing circuits 37 and 38 from being damaged by the defibrillation voltage. The block 46 is a high voltage charge block and contains a high voltage capacitor that is charged to deliver a defibrillating pulse. The defibrillating pulse is delivered from the high voltage delivery block 47 to electrodes 52 and 53 connected to the heart 40 via lines 50 and 51.

The chip IC1 contains an ECG sensing and waveform analysis block 71 which receives ECG heart signals to be monitored and processed. Specifically, the heart signals coming from the atrium are fed to the sensing and waveform analysis block 71 via the line 42. The heart signals coming from the ventricle are fed to the block 71 via the line 44.

The block 71 includes a first three-stage amplifier/filter network for sensing the heart signals in the atrium and a second three-stage amplifier/filter network for sensing the heart signals in the ventricle. A switched capacitor filter stage 10 utilized in the first network or second network is illustrated in detail in FIG. 2 for providing a low charge-injection induced offset voltage on the output of an operational amplifier.

Figure 2:
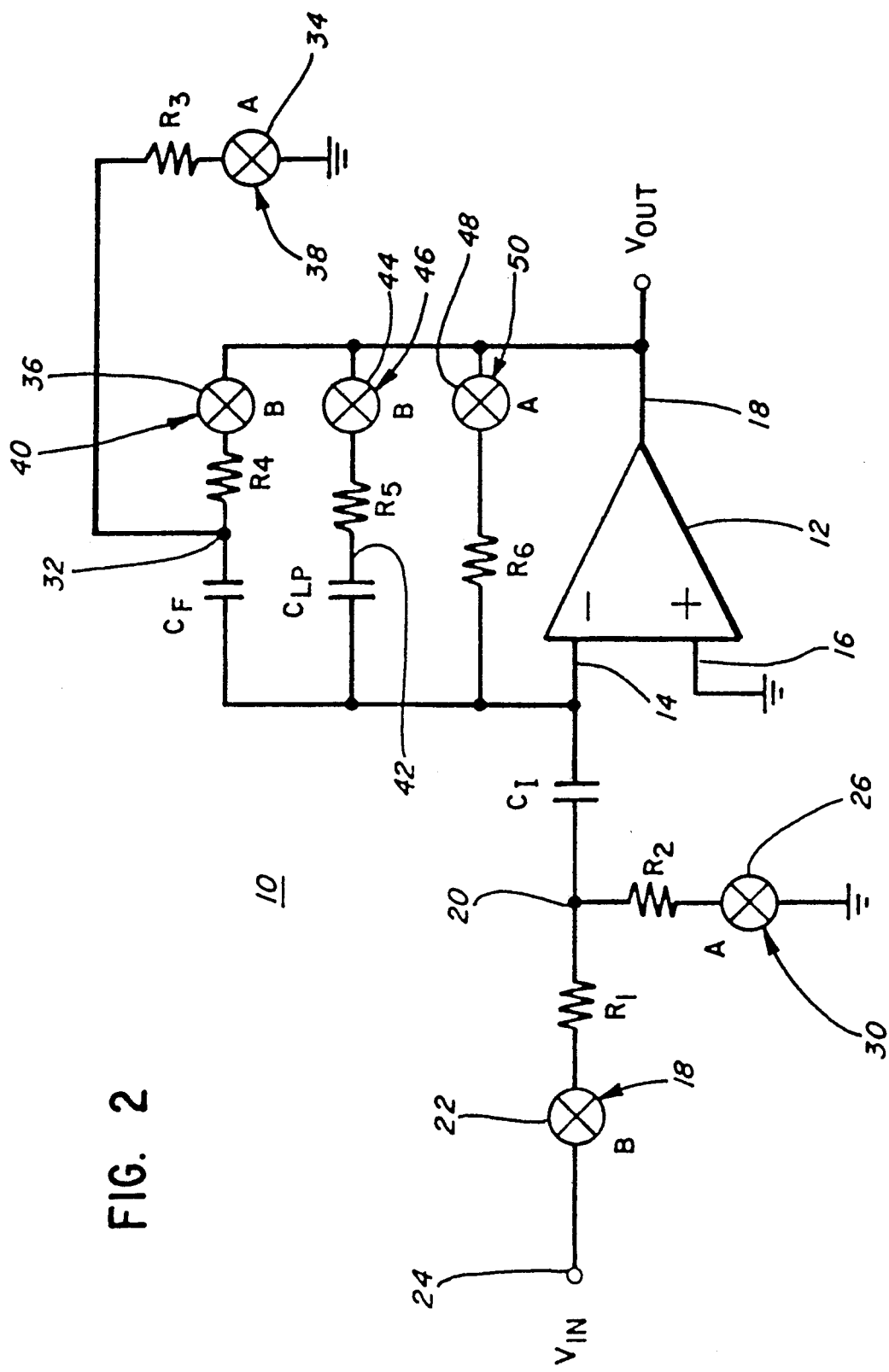
FIG. 2 is a schematic circuit diagram of a switched capacitor filter stage, constructed in accordance with the principles of the present invention.

Referring now in detail to FIG. 2 of the drawings, there is illustrated a schematic circuit diagram of a switched capacitor filter stage 10 constructed in accordance with the principles of the present invention. The filter stage 10 comprises an operational amplifier 12 which has an inverting input terminal 14, a non-inverting input terminal 16, and an output terminal 18. The non-inverting input terminal 16 is connected to a reference voltage VREF shown here as a ground potential.

An input capacitor $C_I$ has its one end connected to a node 20 and its other end connected to the inverting input terminal 14 of the operational amplifier. A transmission gate 22 has its signal input connected to a signal input terminal 24 for receiving an input signal $V_{in}$ and its signal output connected to one end of a charge steering resistor R1. The other end of the resistor R1 is connected to the node 20. A transmission gate 26 has its signal input connected to the ground potential and its signal output connected to one end of a charge steering resistor R2. The other end of the resistor R2 is also connected to the node 20. The control terminal 28 of the transmission gate 22 is connected to receive a control signal $\phi B$, and the control terminal 30 of the transmission gate 26 is connected to receive a control signal $\phi A$.

A feedback capacitor $C_F$ has its one end connected to a node 32 and its other end connected to the inverting input 14 of the operational amplifier. A transmission gate 34 has its signal input connected to the ground potential and its signal output connected to one end of a charge steering resistor R3. The other end of a resistor R3 is connected to the node 32. A transmission gate 36 has its signal input connected to the output terminal 18 of the operational amplifier and its signal output connected to one end of a charge steering resistor R4. The other end of the resistor R4 is connected to the node 32.

The control terminal 38 of the transmission gate 34 is connected to receive the control signal $\phi A$, and the control terminal 40 of the transmission gate 36 is connected to receive the control signal $\phi B$.

A filter capacitor $C_{LP}$ has its one end connected to a node 42 and its other end connected to the inverting input terminal 14 of the operational amplifier. A transmission gate 44 has its signal input connected to the output terminal 18, its signal output terminal connected to one end of a charge steering resistor R5, and its control terminal 46 connected to receive the control signal $\phi B$. The other end of the resistor R5 is connected to the node 42. A transmission gate 48 has its signal input connected to the output terminal 18, its signal output connected to one end of a charge steering resistor R6, and its control terminal 50 connected to receive the control signal $\phi A$. The other end of the resistor R6 is connected to the inverting input terminal 14.

Each of the transmission gates 22, 26, 34, 36, 44 and 48 is a conventional CMOS transmission gate formed of a P-channel MOS transistor and an N-channel MOS transistor with each gate having a signal input, a signal output, a true clock input, and a complementary clock input. The true clock input is connected to the gate electrode of the N-channel transistor, and the complementary clock input is connected to the gate electrode of the P-channel transistor. When the true clock input is at a high or logic "1" level and the complementary clock input is at a low or logic "0" level, a signal applied to the signal input will be coupled to the signal output. Thus, the transmission gate is defined to be closed or turned on. When the true clock input is at a low level and the complementary clock input is at a high level, a signal applied to the signal input will not be coupled to the signal output. Thus, the transmission gate is defined to be opened or turned off.

It will be noted that only the true clock inputs corresponding to the control terminals 28, 30, 38, 40, 46 and 50 of the respective transmission gates have been shown in FIG. 2. Thus, the complementary clock inputs for these transmission gates have been purposely omitted for the sake of clarity. Further, it will be apparent to those skilled in the art that when the transmission gates are turned on they will exhibit a certain amount of resistance. Typically, the resistance value would be on the order of 10K ohms.

Each of the charge steering resistors R1 through R6 is implemented by a pair of CMOS transistors connected as shown in FIG. 4. As can be seen, the channel electrodes of the N-channel transistor N1 are connected in parallel with the channel electrodes of the P-channel transistor P1 and are available on terminals 52 and 54. The gate electrode of the transistor N1 is connected to a positive supply voltage or potential +V, and the gate electrode of the transistor P1 is connected to the ground potential. Thus, the transistors N1, P1, or both, depending on the magnitude of the signal voltage, are always turned on. By designing the transistors N1 and P1 to have a short channel width and a long channel length, a high resistance value can be obtained across the terminals 52 and 54. In order that the stored channel charges in the transmission gates be directed away from the corresponding capacitors whose other ends are tied to a sensitive node (i.e., the inverting input terminal 14 of the operational amplifier), the value of the resistors R1 through R6 are chosen to be in the range of 100K ohms-150K ohms.

FIG. 3(a) illustrates a waveform 56 which represents the periodic control signal φA that is applied to the N-channel control terminals of the respective transmission gates 26, 34 and 48. FIG. 3(b) illustrates a waveform 58 which represents the periodic control signal φB that is applied to the N-channel control terminals of the respective transmission gates 22, 40 and 44. While the control signal φB has the same frequency, it is delayed in such a manner that the control signals φA and φB are non-overlapping and are operated in what is known as a "break-before-make" fashion.

When the control signal φA is active or at the logic "1" level such as between the times t1a and t1b, this is generally referred to as the "auto-zero" phase. When the control signal φB is active such as between the times t3a and t3b this is generally referred to as the "sampling" or "acquiring" phase. Unlike the control signals of the prior art used to control the switched transistors, the waveforms 56 and 58 have a generally trapezoidal shape. Thus, the leading and trailing edges of the control signals φA and φB have been slowed down and do not have the sharp rise and fall times of prior art clock pulses. Typically, the rise and fall times of the control signals φA and φB are on the order of one microsecond.

In FIG. 5(a) there is depicted a schematic circuit diagram of a trapezoidal clock generator 60 for producing the control signal φA having the trapezoidal shape in response to periodic clock pulses PH1A. As can be seen, the trapezoidal clock generator 60 includes an N-channel MOS switching transistor S1, a first current source I1, a P-channel MOS switching transistor S2, a second current source I2, and a storage capacitor $C_{trap}$. It should be apparent to those skilled in the art that a similar generator could be implemented to produce the control signal φB and the complementary control signals $\bar{\phi}A$, $\bar{\phi}B$ having a trapezoidal shape.

The switching transistor S1 has its drain connected to one end of the first current source I1 and its source connected to the ground potential. The other end of the first current source I1 is connected to an output node 62 for producing the control signal φA. The storage capacitor $C_{trap}$ is connected between the output node 62 and the ground potential. The switching transistor S2 has its source connected to a supply potential VDD and its drain connected to one end of the second current source I2. The other end of the second current source I2 is connected to the output node 62. The gates of the switching transistors S1 and S2 are joined together into an input node 64 for receiving the periodic clock pulses PH1A.

FIG. 5(b) illustrates a pulse 65 of periodic clock pulses PH1A. FIG. 5(c) illustrates a pulse 66 of the control signal φA, which has been enlarged over the ones of FIG. 3(a) to show the rise and fall times. When the clock pulse 65 is at a low logic level, the switching transistor S1 is turned off and the switching transistor S2 is turned on. As a result, the second current source I2 will be allowed to charge up the storage capacitor $C_{trap}$ to produce the rising edge 68 of the pulse 66. When the clock pulse 65 is at a high logic level, the switching transistor S2 is turned off and the transistor S1 is turned on. Therefore, the storage capacitor will be allowed to discharge through the first current source I1 to produce the falling edge 70 of the pulse 66.

The operation of the switched capacitor filter stage 10 will now be explained with reference to the waveform diagrams of FIGS. 3(a)–3(d). Initially, it will be assumed that prior to the time tφ all of the capacitors $C_I$, $C_F$ and $C_{LP}$ have been completely discharged. A ramp input signal $V_{in}$ is applied to the signal input terminal 24 at the time tφ, as illustrated in FIG. 3(c). At the time t1, the control signal φA will begin to slowly make a low-to-high transition between the times t1 and t1a and the control signal φB will remain at the low logic level. The control signals φA and φB are illustrated in respective FIGS. 3(a) and 3(b). During the "auto zero" phase between the times t1a and t1b, the transmission gates 26, 34 and 48 are closed so as to discharge the capacitors $C_I$ and $C_F$, and the transmission gates 28, 36 and 44 are opened.

The filter capacitor $C_{LP}$ will hold the charge between the times t1a and t1b. Further, since the inverting terminal of the op-amp is coupled to the output of the op amp, the output terminal 18 will be at the stage input offset voltage, as illustrated in FIG. 3(d). Between the times t1b and t2, the control signal φA will slowly make a high-to-low transition so as to gradually turn off the transmission gates 26, 34 and 50, thereby reducing clock feedthrough. If the charge steering resistors R2, R3 and R6 were not present, the stored channel charges in the transmission gates 26, 34 and 50 when they are turned off would still cause a voltage to be coupled via the capacitors $C_I$ and $C_F$ to the sensitive node at the inverting input terminal 14 of the operational amplifier, thereby producing an output offset voltage during the acquiring phase. However, due to the insertion of the relatively large resistance values of the resistors R2, R3 and R6 the stored channel charges are directed away from the sensitive node.

After a short delay, the control signal φB will slowly make a low-to-high transition between the times t3 and t3a. During the "sampling" phase between t3a and t3b, the transmission gates 26, 34 and 50 are opened, and the transmission gates 28, 36 and 44 are closed so as to permit the initial charging of capacitors $C_I$, $C_F$, and $C_{LP}$ up to the applied input voltage. Between the times t3b and t4, the control signal φB will slowly make a high-to-low transition so as to gradually turn off the transmission gates 22, 40 and 44, thereby reducing clock feedthrough. Similarly, if the charge steering resistors R1, R4 and R5 were not present, the stored channel charges in the transmission gates 22, 40 and 44 when they are turned off would still cause a voltage to be coupled via the capacitors $C_I$, $C_F$ and $C_{LP}$ to the sensitive node, thereby generating an offset voltage on the output terminal 18. However, due to the insertion of the relatively large resistance values of the resistors R1, R4 and R5, the stored channel charges are again directed away from the sensitive node.

From the foregoing detailed description, it can thus be seen that the present invention provides an implantable cardiac defibrillator which employs a switched capacitor filter stage which includes a unique switch structure so as to produce a low charge-injection induced offset voltage on the output of an operational amplifier. Charge steering resistors are connected in series with corresponding switched capacitors that are coupled to a sensitive node of the operational amplifier. The switches associated with the switched capacitors are operated by control signals having a generally trapezoidal shaped waveform so as to slowly turn them off.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. A clock generator for generating a trapezoidal clock waveform comprising:
    first MOS switch means having a first end and a second end;
    first current source means having a first end connected to the first end of said first switch means and a second means connected to an output node;
    second MOS switch means having a first end and a second end;
    second current source means having a first end connected to the first end of said second switch means and a second end connected to the output node;
    the second end of said second MOS switch means being connected to an upper supply potential and the second end of said first MOS switch means being connected to a lower supply potential;
    said first and second MOS switch means being responsive to a periodic control signal for turning on and off same; and
    capacitor means coupled between the output node and the lower supply potential and being responsive to said first and second MOS switch means for producing a trapezoidal clock waveform.

2. A clock generator as claimed in claim 1, wherein said first MOS switch means comprises an N-channel MOS transistor.

3. A clock generator as claimed in claim 1, wherein said second MOS switch means comprises a P-channel MOS transistor.

4. A clock generator as claimed in claim 1, wherein said first current source means comprises a first current source.

5. A clock generator as claimed in claim 2, wherein said second current source means comprises a second current source.

6. A clock generator as claimed in claim 1, wherein said capacitor means comprises a capacitor.

* * * * *